(12) United States Patent
Savidge et al.

(10) Patent No.: US 10,501,771 B2
(45) Date of Patent: Dec. 10, 2019

(54) METHODS AND USES FOR METABOLIC PROFILING FOR *CLOSTRIDIUM DIFFICILE* INFECTION (71) Applicant: The Board of Regents of the University of Texas System, Austin, TX (US)

(72) Inventors: Tor Savidge, League City, TX (US); Sara Dann, Galveston, TX (US)

(73) Assignee: THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 1443 days.

(21) Appl. No.: 14/357,027

(22) PCT Filed: Nov. 8, 2012

(86) PCT No.: PCT/US2012/064218
§ 371 (c)(1),
(2) Date: May 8, 2014

(87) PCT Pub. No.: WO2013/070962
PCT Pub. Date: May 16, 2013

(65) Prior Publication Data
US 2014/0296134 A1 Oct. 2, 2014

Related U.S. Application Data (60) Provisional application No. 61/557,383, filed on Nov. 8, 2011.

(51) Int. Cl.
*C12Q 1/04* (2006.01)
*G01N 33/68* (2006.01)
*G01N 33/569* (2006.01)

(52) U.S. Cl.
CPC ......... *C12Q 1/04* (2013.01); *G01N 33/56905* (2013.01); *G01N 33/6893* (2013.01); *G01N 2333/33* (2013.01); *G01N 2560/00* (2013.01); *G01N 2800/26* (2013.01)

(58) Field of Classification Search
None
See application file for complete search history.

(56) References Cited

U.S. PATENT DOCUMENTS

| 7,306,953 B2 | 12/2007 | Probert et al. | 436/181 |
| 2010/0317681 A1 | 12/2010 | Forbes | 514/183 |
| 2011/0117154 A1 | 5/2011 | Sayada | 424/405 |
| 2012/0040383 A1 | 2/2012 | Jia et al. | 435/12 |

FOREIGN PATENT DOCUMENTS

WO WO 2009/035497 3/2009

OTHER PUBLICATIONS

Chen et al, Mol. Syndromol. 5:299-303, 2014.*
Gerding, "Treatment of Clostridium difficile-associated diarrhea and colitis", *Curr Top Microbiol Immunol,* 250: 127-39, 2000.
McFarland et al., "A randomized placebo-controlled trial of *Saccharomyces boulardii* in combination with standard antibiotics for Clostridium difficile disease", *JAMA,* 271(24): 1913-8, 1994.
International Search Report and Written Opinion issued in PCT/US12/64218, dated Mar. 20, 2013.
Kyoto Encyclopedia of Genes and Genomes. Arginine and Proline Metabolism—Clostridium Difficile 630, [organism added Mar. 29, 2007 <URL: http://www.genome.jp/kegg/docs/updnote.html>; map archived Sep. 19, 2011 <URL: http://web.archive.org/web/20110919185405/http://www.genome.jp/kegg/pathway/map/map00330.html>] [online], [retrieved on Jan. 15, 2011]. Retrieved from the internet: <URL: http://www.genome.jp/kegg-bin/show_pathway?cdf00330>.
Barroso, "Effect of Autoregulated TxeR On The Expression of Clostridium Difficile Toxins", Dec. 1, 1999 [online] [retrieved on Jan. 12, 2012]. Retrieved from the internet: <URL: http://scholar.lib.vt.edu/theses/avaliable/etd-120699-141047/unrestricted/CompleteThesis.pdf>, p. 28, paragraph 2-p. 29, paragraph 1.
Tang-Feldman et al., "Molecular Analysis of Clostridium Difficile Strains Isolated from 18 Cases of Recurrent Clostridium Difficile-Associated Diarrhea", *Journal of Clinical Microbiology,* 41(7): 3413-3414, 2003.
Sebaihia et al., "The Multidrug-Resistant Human Pathogen Clostridium Difficile Has a Highly Mobile, Mosaic Genome", *Nature Genetics,* 38: 779-86, 2006.
Everly, "Characterization of Microorganisms Of Interest To Homeland Security And Public Health Utilizing Liquid Chromatography/Mass Spectrometry", May 2008 [online] [retrieved on Dec. 1, 2013]. Retrieved from the internet: <URL: https://dizzyg.library.vcu.edu/bitstream/handle/10156/1766/everleyra_phd.pdf?sequence=1>.
Choi, HK et al., "Risk Factors For Recurrence Of Clostridium Difficile Infection: Effect Of Vancomycin-Resistant Enterococci Colonization", *Journal of Korean Academy of Medical Sciences,* 26(7): 859-864, 2011.
Bezabeh et al. "MR metabolomics of fecal extracts: applications in the study of bowel diseases" Magn. Reson. Chem 47:S54-S61, 2009.
Boone JH et al. "Elevated lactoferrin is associated with moderate to severe Clostridium difficile disease, stool toxin, and 027 infection" Eur J Clin Microbiol Infect Dis 32:1517-23, 2013.
Garner CE et al. "Volatile organic compounds from feces and their potential for diagnosis of gastrointestinal disease" FESEB 21:1675-88, 2007.
Probert CSJ et al. "A novel method for rapidly diagnosing the causes of diarrhoea" Gut 53:58-61, 2004.
International Preliminary Report on Patentability issued in PCT/US2012/064218, dated May 13, 2014.

* cited by examiner

*Primary Examiner* — Brian Gangle
(74) *Attorney, Agent, or Firm* — Norton Rose Fulbright US LLP (57) ABSTRACT

Embodiments include methods for generating a metabolite profile of a stool sample and methods of assessing the status of a subject using the metabolic profile derived from a stool sample.

6 Claims, 7 Drawing Sheets

METHODS AND USES FOR METABOLIC PROFILING FOR *CLOSTRIDIUM DIFFICILE* INFECTION

This application is a national stage application of international application PCT/US2012/064218 filed Nov. 8, 2012, which claims priority to U.S. Provisional application Ser. No. 61/557,383 filed Nov. 8, 2011. Priority is claimed to each application and each application is incorporated herein by reference in its entirety.

This invention was made with government support under 1UL1RR029876-01 and AI10094001 awarded by the National Institutes of Health, National Heart Lung and Blood Institute, and Immunity, Allergy and Infectious Diseases. The government has certain rights in the invention.

TECHNICAL FIELD

Embodiments are directed to the general field of microbiology, medicine, and medical diagnostics.

BACKGROUND

*C. difficile* is a gram-positive, spore forming anaerobic bacterium that is the primary causative agent for pseudomembranous colitis and bacterial-induced diarrhea. *C. difficile* is rapidly emerging as a nosocomial pathogen in health care facilities around the world with an estimated 1 to 3% of all hospitalized patients under antibiotic treatment becoming infected with *C. difficile*. Even more alarming, a recent outbreak of a more virulent strain of *C. difficile* was correlated with the death of more than 100 patients within a 6-month period in a single hospital.

In the U.S., *Clostridium difficile* infection (CDI) is one of the most prolific causes of bacterial-induced diarrhea. Up to 3 million cases are estimated annually at a cost greater than $3.5 billion, with infection rates in some hospitals approaching 40%. In the last 15 years, the incidence of CDI has more than doubled. This increase is largely due to the emergence of a new hypervirulent strain (BI/NAP1/027) that releases pathogenic exotoxins, causing colonic inflammation and fluid secretion. Despite a known correlation between antimicrobial disruption of protective gut microflora and the development of symptoms in infected individuals, there is still a major gap in our understanding of why certain patients are susceptible to disease by this pathogen. Readily available treatment options for CDI include metronidazole and vancomycin, but both drugs are associated with relapse rates as high as 35%. Disease recurrence increases further (up to approximately 50%) in subsequent infective episodes, often necessitating surgical intervention. Thus, disease relapse represents the most significant clinical issue in CDI, and there is an urgent need to identify and prophylactically manage high-risk patients.

Given the complex genetic, proteomic, and environmental interactions that appear to be involved in CDI there is a need to develop a comprehensive categorization of subjects based on molecular and phenotypic variables. More specifically, there is a need to categorize functional metabolites in patient samples as biomarkers of clinical phenotype, activity, and treatment.

DISCLOSURE

Metabolomics refers to the study of the complete set of metabolites (the metabolome) in a biological sample under a given set of conditions. Unlike its commonly used screening counterparts (genomics and proteomics), the metabolome is highly responsive to pathophysiological conditions, thus making it ideally suited to distinguish subtle disease phenotypes. The inventors have been able to successfully identify biochemical profiles in clinical specimens that classify CDI with a high degree of confidence. Furthermore, the inventors have identified biochemical profiles in clinical stool specimens that identify susceptibility to disease recurrence. In certain aspects, methods apply bipartite network analysis of the metabolome. This unique technique uses visual analytical approaches to discover and validate patterns in biomedical data, and translate those discoveries into clinical practice. The metabolic profile can be used to assess various physiological processes. In one aspect a metabolic profile is derived from a stool sample. Metabolic profiles can be used to evaluate various organ systems and the physiologic state of a subject at a given time. In certain aspects, the metabolic profile can be diagnostic or prognostic of a number of pathological conditions. In certain embodiments a metabolic profile can identify a subject with CDI or who has or is at risk for recurrent CDI.

In certain embodiments a metabolic profile indicative of a pathological condition includes measurement of one or more of 5-aminovalerate, thymine, gamma-aminobutyrate (GABA), ammonia, N-acetylglutamate, agmatine, serine, N-acetylmuramate, X-16563, X-16071, X-15461 and X-15175.

In certain embodiments a metabolic profile indicative of a pathological condition includes measurement of one or more of 5-aminovalerate, thymine, gamma-aminobutyrate (GABA), ammonia, N-acetylglutamate, agmatine, serine, and N-acetylmuramate.

In certain aspects 5-aminovalerate is measured in combination with one or more of thymine, gamma-aminobutyrate (GABA), ammonia, N-acetylglutamate, agmatine, serine, N-acetylmuramate, X-16563, X-16071, X-15461 and X-15175.

In certain aspects 5-aminovalerate is measured in combination with one or more of thymine, gamma-aminobutyrate (GABA), ammonia, N-acetylglutamate, agmatine, serine, N-acetylmuramate.

In a further aspect one or more of 5-aminovalerate and thymine are measured in combination with one or more of gamma-aminobutyrate (GABA), ammonia, N-acetylglutamate, agmatine, serine, N-acetylmuramate, X-16563, X-16071, X-15461 and X-15175.

In a further aspect one or more of 5-aminovalerate and thymine are measured in combination with one or more of gamma-aminobutyrate (GABA), ammonia, N-acetylglutamate, agmatine, serine, and N-acetylmuramate.

In a further aspect one or more of 5-aminovalerate, thymine, and gamma-aminobutyrate (GABA) are measured in combination with one or more of ammonia, N-acetylglutamate, agmatine, serine, N-acetylmuramate, X-16563, X-16071, X-15461 and X-15175.

In a further aspect one or more of 5-aminovalerate, thymine, and gamma-aminobutyrate (GABA) are measured in combination with one or more of ammonia, N-acetylglutamate, agmatine, serine, and N-acetylmuramate.

In a further aspect one or more of 5-aminovalerate, thymine, gamma-aminobutyrate (GABA), and ammonia are measured in combination with one or more of N-acetylglutamate, agmatine, serine, N-acetylmuramate, X-16563, X-16071, X-15461 and X-15175.

In a further aspect one or more of 5-aminovalerate, thymine, gamma-aminobutyrate (GABA), and ammonia are measured in combination with one or more of N-acetylglutamate, agmatine, serine, and N-acetylmuramate.

In a further aspect one or more of 5-aminovalerate, thymine, gamma-aminobutyrate (GABA), ammonia, and N-acetylglutamate are measured in combination with one or more of agmatine, serine, N-acetylmuramate, X-16563, X-16071, X-15461 and X-15175.

In a further aspect one or more of 5-aminovalerate, thymine, gamma-aminobutyrate (GABA), ammonia, and N-acetylglutamate are measured in combination with one or more of agmatine, serine, and N-acetylmuramate.

In a further aspect one or more of 5-aminovalerate, thymine, gamma-aminobutyrate (GABA), ammonia, N-acetylglutamate, and agmatine are measured in combination with one or more of serine, N-acetylmuramate, X-16563, X-16071, X-15461 and X-15175.

In a further aspect one or more of 5-aminovalerate, thymine, gamma-aminobutyrate (GABA), ammonia, N-acetylglutamate, and agmatine are measured in combination with one or more of serine and N-acetylmuramate.

In a further aspect one or more of 5-aminovalerate, thymine, gamma-aminobutyrate (GABA), ammonia, N-acetylglutamate, agmatine, and serine are measured in combination with one or more of N-acetylmuramate, X-16563, X-16071, X-15461 and X-15175.

In a further aspect one or more of 5-aminovalerate, thymine, gamma-aminobutyrate (GABA), ammonia, N-acetylglutamate, agmatine, and serine are measured in combination with N-acetylmuramate.

In a further aspect one or more of 5-aminovalerate, thymine, gamma-aminobutyrate (GABA), ammonia, N-acetylglutamate, agmatine, serine, and N-acetylmuramate are measured in combination with one or more of X-16563, X-16071, X-15461 and X-15175.

In a further aspect one or more of 5-aminovalerate, thymine, gamma-aminobutyrate (GABA), ammonia, N-acetylglutamate, agmatine, serine, N-acetylmuramate, and X-16563 are measured in combination with one or more of X-16071, X-15461 and X-15175.

In a further aspect one or more of 5-aminovalerate, thymine, gamma-aminobutyrate (GABA), ammonia, N-acetylglutamate, agmatine, serine, N-acetylmuramate, X-16563, and X-16071 are measured in combination with one or more of X-15461 and X-15175.

In a further aspect, a pathological condition can be gastrointestinal conditions including *Clostridium difficile* infection (CDI).

In certain aspects non-infected subjects can be distinguished from subjects at risk of recurrent CDI by assessing the levels of one or more of 5-aminovalerate, thymine, gamma-aminobutyrate (GABA), ammonia, X-16563, and/or X-16071. In certain aspects, the levels of the measured biomarkers are elevated.

In a further aspect, non-infected subjects can be distinguished from subjects having a non-recurrent CDI by assessing the levels of one or more of 5-aminovalerate, N-acetylglutamate, thymine, X-15461, and/or X-15175. In certain aspects, the levels of the measured biomarkers are elevated.

In still a further aspect, subjects having a non-recurrent infection can be distinguished from subjects having or at risk of having a recurrent infection by assessing the levels of X-14400, agmatine, pyruvate, tryptamine, ammonia, gamma-aminobutyrate (GABA) and/or beta-hydroxyisovalerate. In certain aspects, the levels of the measured biomarkers are elevated. In certain aspects, a more aggressive or prophylactic treatment is administered to those subjects identified as having or being at risk of recurrent infection.

The term "elevated" refers to a statistically significant difference (e.g., an increase of at least 5%, 10%, 20%, 25%, 35%, 40%, 45%, 50%, 55%, 60%, 65%, 70%, 75%, 80%, 85%, 90%, 95%, 100%, 120%, 140%, 160%, 180%, 200%, 220%, 240%, 260%, 280%, or 300% increase or more) in a measured level compared to a reference level. The term "decreased" refers to a statistically significant difference (e.g., a decrease of at least 5%, 10%, 20%, 25%, 35%, 40%, 45%, 50%, 55%, 60%, 65%, 70%, 75%, 80%, 85%, 90%, 95%, 100%, 120%, 140%, 160%, 180%, 200%, 220%, 240%, 260%, 280%, or 300% decrease or more) in a determined or measured level compared to a reference level. The term "reference level" means a threshold level or a level in a control subject, a control population, or an average of control population, or a level previously measured in the same individual. A reference level will depend on the assay performed and can be determined by one of ordinary skill in the art. The reference level can be used to distinguish subjects having and not having a condition or disease, e.g., CDI.

In certain aspects a biological sample can be a stool, urine, or blood sample. In further aspects the biological sample is a stool sample. In still further aspects the stool sample can be obtained from a subject having or has recently had diarrhea (within 1, 2, 3, 4, 5, 6, 7, 8, 9, 10, 11, 12, hours or days).

In certain aspects, methods are directed to the identification of accurate metabolomic stool biomarkers for a gastrointestinal condition, e.g., CDI, and translation of these findings into effective diagnostic, prognostic, and/or nutraceutical therapies.

In a further aspect analysis of the stool metabolome is used to identify subjects having an increased risk of disease relapse or recurrence of CDI. Assessment of disease progression and relapse is based on the concept that gut microbe composition is an important determinant in whether CDI patients are susceptible to relapse. In other aspects, network and disease classification analysis of the stool metabolome has identified highly significant differences in biochemical profiles that enable positive-categorization of CDI patients from other cases of antibiotic-associated diarrhea with a high degree of confidence. Increases or decreases in metabolites related to bacterial activity and inflammation are evident in CDI patients, e.g., altered nitrogen metabolism, bile acid conjugation, and polyamine metabolism. The pathophysiological relevance of a metabolomics approach in CDI is supported by highly significant changes recorded in nitrogen-based metabolite and dietary cofactor regulators of *C. difficile* virulence.

Other aspects are directed to a method for identifying and/or selecting a prophylactic dietary supplement therapy for the treatment of microbial infections. In certain aspects methods of treating *C. difficile* infection comprises providing phytic acid supplements or stable phytic-acid derivatives.

Current FDA-approved diagnostic assays for CDI are limited by their cost, technical complexity, long assay duration and/or sensitivity. No diagnostic assays currently exist that predict disease relapse in CDI, and these are urgently warranted. In certain aspects, methods are directed to measurement of a stool metabolome of CDI patients to identify and predict patterns of disease progression and relapse.

In a further aspect, cross-validated out-of-sample error rate and bipartite network analysis of metabolomics data has demonstrated excellent disease classification for cytotoxicity-confirmed CDI. In certain aspects, the inventors can demonstrate the ability to predict symptomatic CDI with an accuracy of at least or about 76, 78, 80, 82, 84, 86, 88, 90, 92, 94, 96, 98, or 99%, including all values and ranges there between.

In certain aspects, assessment of the biomarkers described herein can provide an analysis with a misclassification rate of 24% between non-infected and CDI infected patients. Analysis of recurrent versus non-recurrent CDI can be determined with a misclassification rate of 39%. Disease relapse within 6 weeks can be determined in 61% of patients at the time of original diagnosis.

Other embodiments of the invention are discussed throughout this application. It is contemplated that any embodiment discussed herein can be implemented with respect to any method or composition of the invention, and vice versa. Furthermore, compositions and kits of the invention can be used to achieve methods of the invention.

The use of the term "detecting" refers to determining the presence, absence, or amount of an analyte in a sample, and can include quantifying the amount of the analyte in a sample.

As used herein "diagnostic" refers to identifying the presence or nature of a pathologic condition. Diagnostic methods differ in their specificity and sensitivity. While a particular diagnostic method may not provide a definitive diagnosis of a condition, it suffices if the method provides a positive indication that aids in diagnosis.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
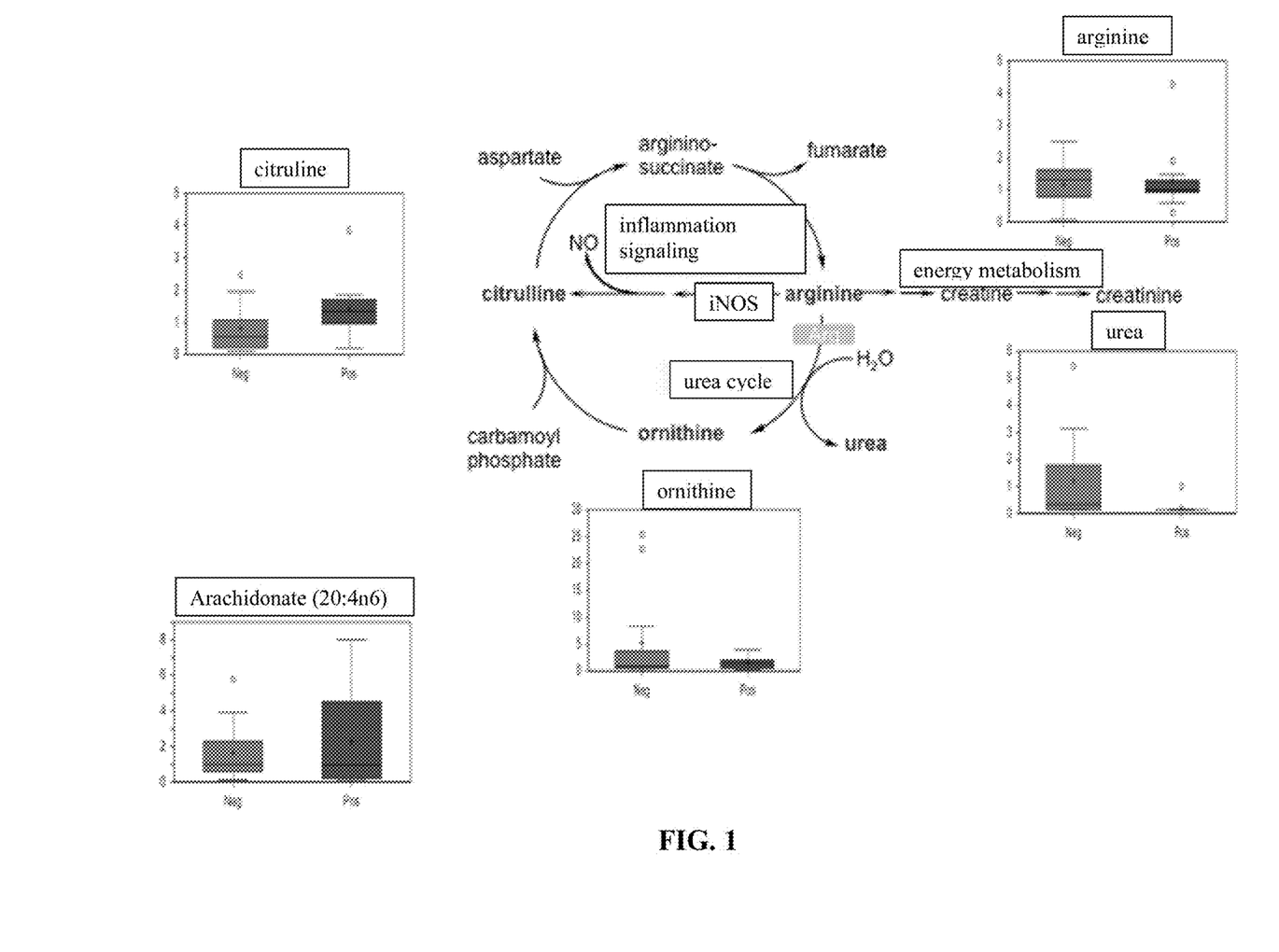
FIG. 1. Arginine Metabolism. *C. difficile* is known to be the primary causative agent for pseudomembranous colitis, and indicators of inflammation including elevated levels of citrulline and arachidonate were observed in the positive samples.
Figure 2A:
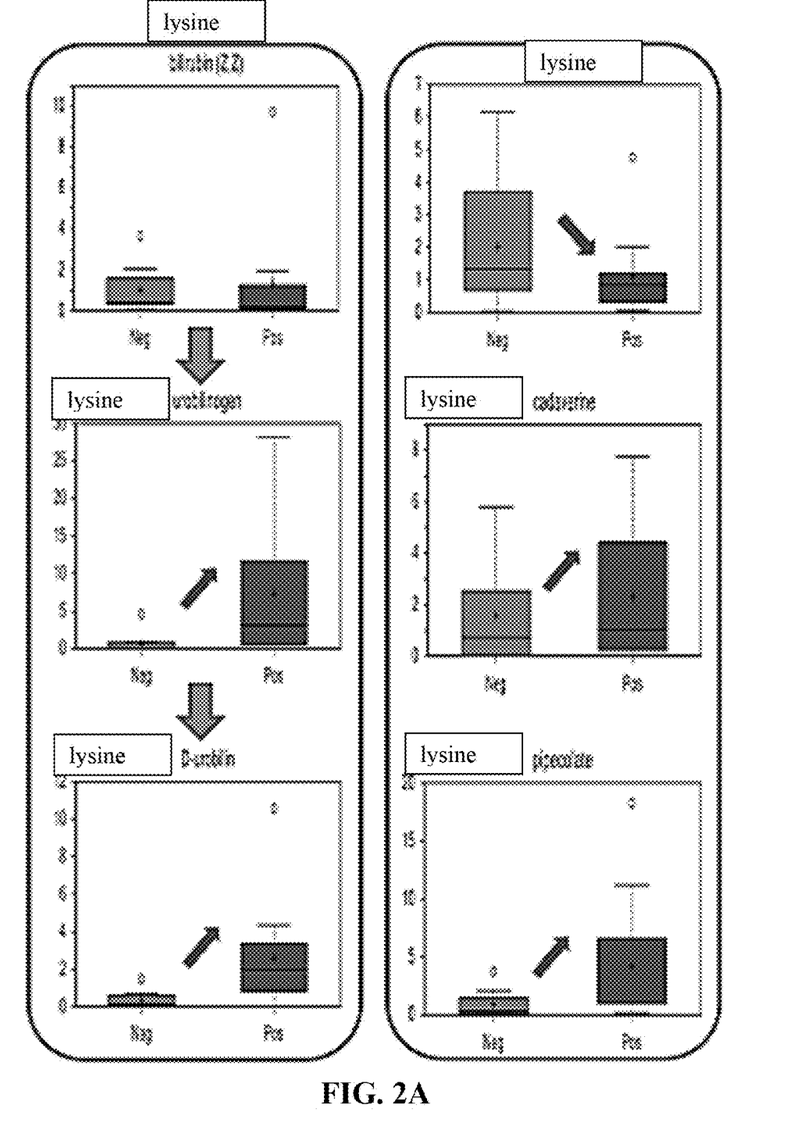
FIGS. 2A and 2B. Indications of Increased Bacterial Metabolism in *C. difficile*-Positive Subjects. (A) Elevated levels of bilirubin metabolites urobilinogen as well as L and D-urobilin may represent increased bacterial activity especially from *C. difficile*. (B) 5-fold lower levels of urea in the positive subjects with increased levels of stool ammonia is an indication of higher levels of bacterial urease activity. Higher levels of lysine metabolites pipecolate and cadaverine may reflect increased intestinal bacterial metabolism in the *C. difficile* positive subjects.
Figure 2B:
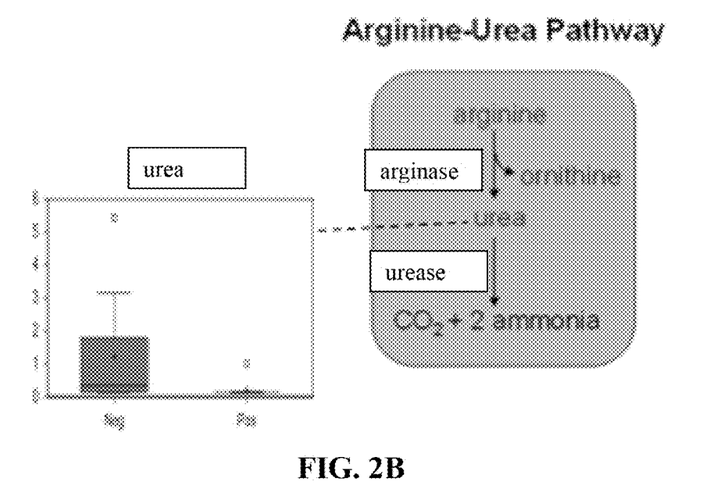
Figure 3:
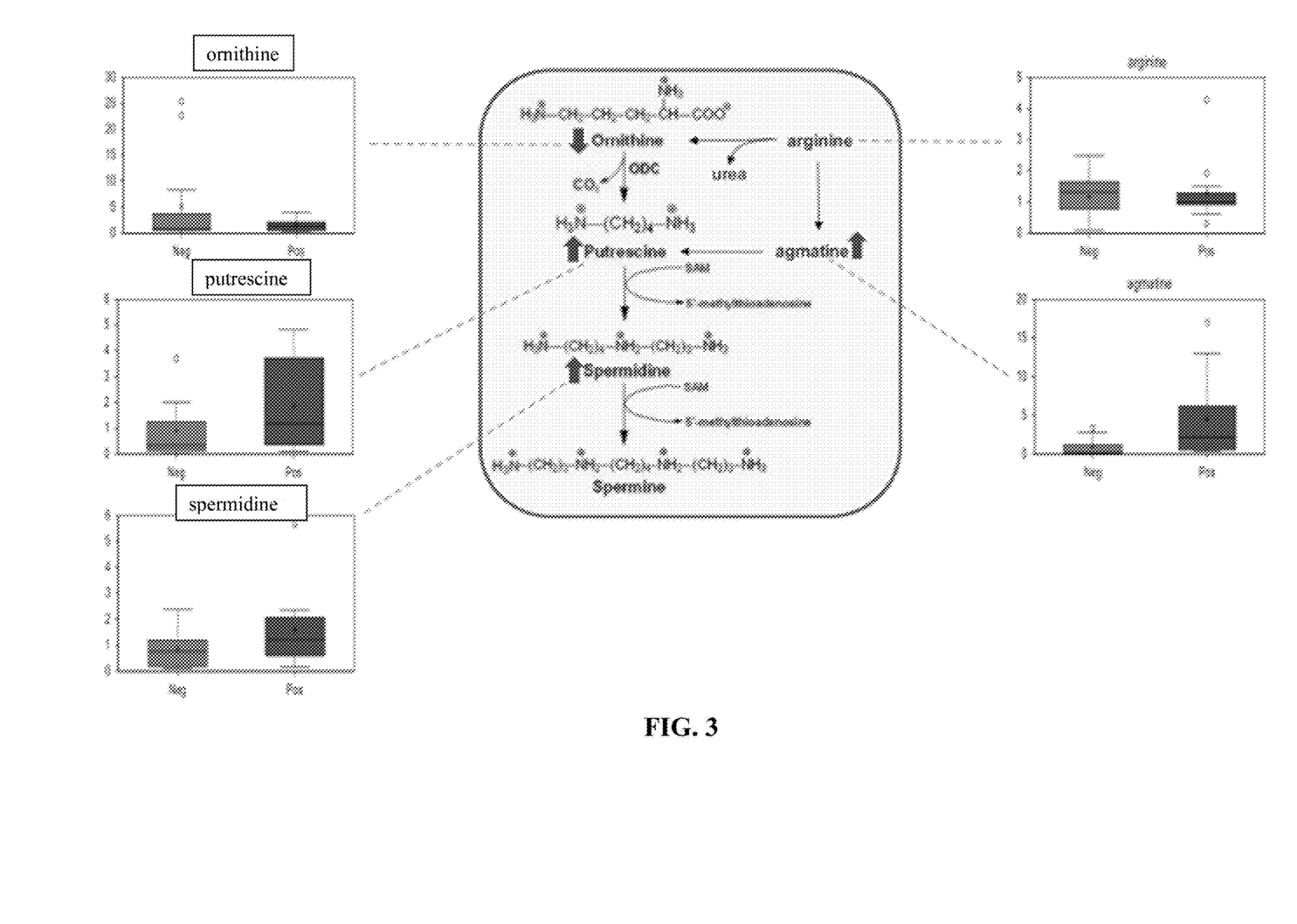
FIG. 3. Polyamines. Extensive data in a wide range of organisms point to the importance of polyamine homeostasis for growth, and two common polyamines found in bacteria, putrescine and agmatine, were higher in the *C. difficile* positive samples. Investigations into polyamine function in bacteria has revealed that they are involved in a number of functions other than growth, which include incorporation into the cell wall and biosynthesis of siderophores associated with the accumulation of iron. They are also important in acid resistance and can act as a free radical ion scavenger. The depletion of the polyamine precursors ornithine and arginine in conjunction with the elevation of polyamines in the positive subjects may further indicate increased bacterial activity in the positive samples.
Figure 4:
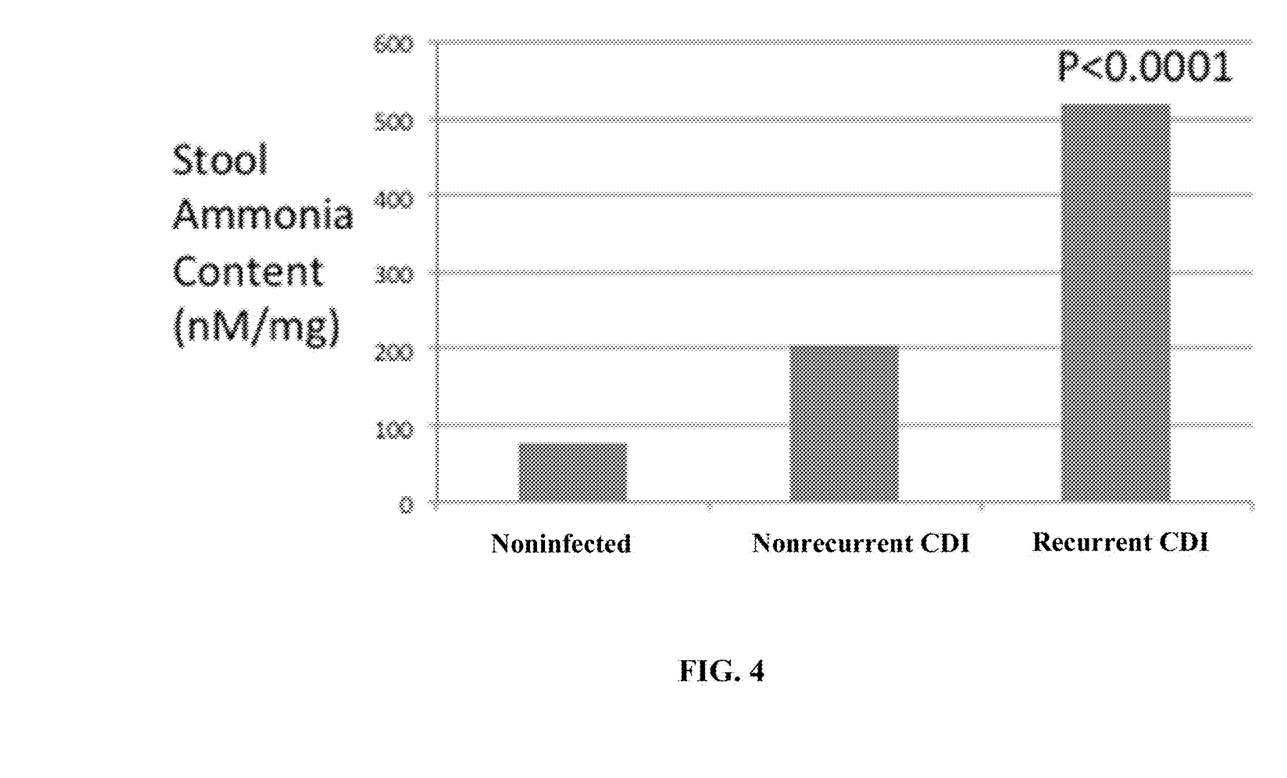
FIG. 4. Illustration of ammonia content of stool in non-infected, non-recurrent CDI, and recurrent CDI.
Figure 5:
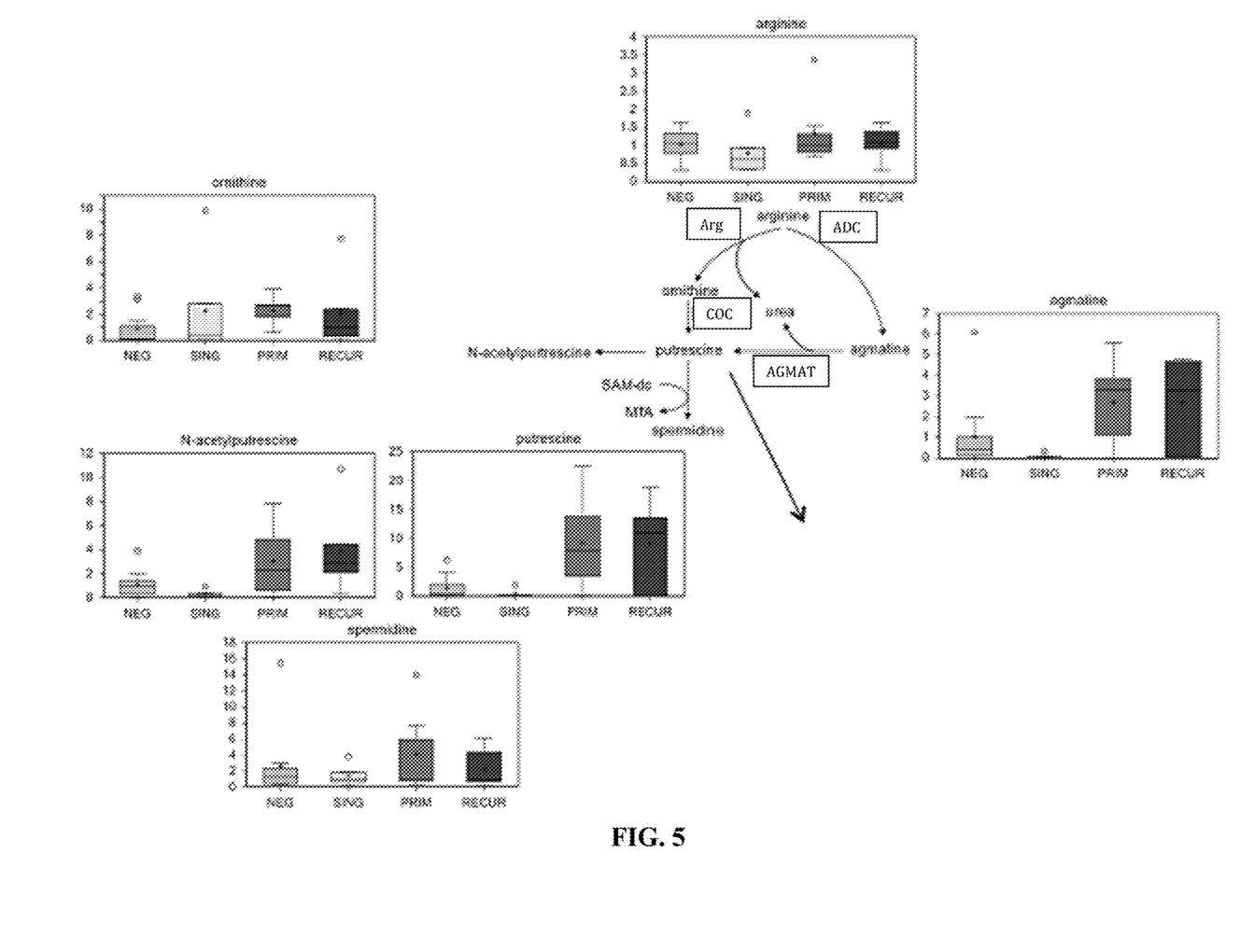
FIG. 5. Polyamines and GABA signatures in recurrent CDI.
Figure 6:
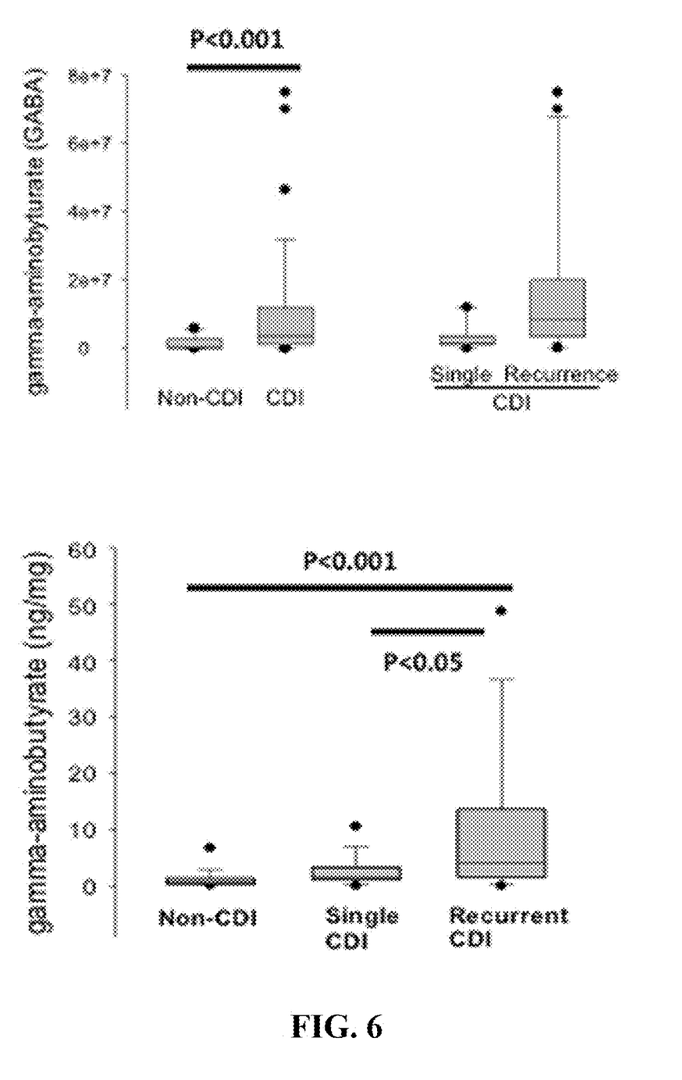
FIG. 6. Neurotransmitter GABA is upregulated in recurrent CDI.

Anaerobic bacteria, i.e., those that grow in oxygen-depleted environments, such as the intestines of a mammal, are important to the well being of the mammal. Gram-positive anaerobes, such as *Lactobacilli, Bifidobacteria*, and *Eubacteria*, and Gram-negative anaerobes, such as *Bacteroides*, represent "good" intestinal organisms, whereas the Gram-positive anaerobe *Clostridium difficile* is a pathogenic bacterium. *Clostridium difficile* (*C. diff*) has been increasingly associated with disease in human patients, ironically often as a result of treatment with certain antibiotic drugs. The most common disease is referred to as *C. diff*-associated diarrhea (CDAD). The inventors describe the use of network analysis of the metabolome to provide a diagnostic approach for identifying and classifying *C. diff* infection (CDI) in a subject.

Certain embodiments include the identification and/or categorization of metabolite profiles in stool samples (the stool metabolome) and identification of certain aspects of the metabolite profile as biomarkers of pathology, clinical phenotype, activity, and/or treatment. The inventors have identified metabolomic stool biomarkers in subjects with pathological conditions, such as gastrointestinal conditions or symptoms thereof. In certain aspects, the subjects present with symptomatic colonic inflammation or microbial infection. In certain aspects the levels of biomarkers measured are used for analysis of disease classification, diagnosis, or prognosis.

Based on recent findings, the concept is that the stool metabolome can be used to predict disease type and progression in subjects, such as CDI patients. The concept is based on the rationale that gut microbe composition (and dietary factors) are important determinants in whether subjects have certain conditions, are susceptible to certain conditions, or are susceptible to relapse of such a condition. The biochemical pathways regulated by, and those pathways not regulated by infecting microbes can cause alterations in a subject's metabolic profile.

Network analysis of the stool metabolome has identified highly significant differences in biochemical profiles that have enabled the inventors to positively categorize patients with *Clostridium difficile* infection from other cases of antibiotic-associated diarrhea with a high degree of confidence. Increases in metabolites related to elevated inflammation and bacterial activity were evident. Novel, unexpected findings were also identified, and were associated with altered nitrogen metabolism, bile acid conjugation, and polyamine metabolism. Translational relevance of this metabolomics approach was demonstrated by showing highly significant changes in virulence factors.

Certain aspects include methods comprising one or more of (a) identifying patterns in the stool metabolome across subjects having a condition and controls—in certain aspect the patterns can be identified using network visualization and analysis; (b) verifying the patterns through graph-based and biostatistical methods; and (c) translating the patterns into new approaches for classifying subjects based on predictive models. In still further aspects, the stool metabolome and alterations in the stool metabolome can be used in identifying drug targets based on the inferred biological pathways.

I. BIOMARKERS

Metabolites identified in the metabolome are used as biomarkers. The term "biomarker", as used herein, refers to a molecule or molecular species (such as a metabolite) used to indicate or measure a biological process. Detection and analysis of a biomarker specific to a disease can aid in the identification, diagnosis, and treatment of the disease, or act as a prognostic marker for the disease. In certain aspects, biomarkers related to CDI include, but are not limited, to metabolites associated with nitrogen metabolism (e.g., ammonia and GABA), polyamine metabolism (e.g., putrescine and agmatine), bile acid metabolites, bilirubin metabolism, and bacterial N-acetylation of several metabolite classes.

Increase in Nitrogen Metabolites.

Nitrogen is a critical chemical element in both proteins and DNA, and thus every living organism must metabolize nitrogen to survive. The urea cycle (also known as the ornithine cycle) is a cycle of biochemical reactions occurring in many animals that produces urea (($NH_2$)$_2$CO) from ammonia ($NH_3$).

Ammonia.

Ammonia is a metabolic product of amino acid deamination catalyzed by enzymes such as glutamate dehydrogenase 1. In humans, ammonia is quickly converted to urea, which is much less toxic. This urea is a major component of the dry weight of urine.

Decreased Urea.

Lower levels of urea in the positive subjects may be an indication of elevated levels of urease activity, which catalyzes the hydrolysis of urea to ammonia and carbon dioxide. Ureases are associated with bacteria and yeast, so the significantly lower urea levels would also be consistent with increased bacterial activity.

Increase in Polyamines.

The depletion of the polyamine precursors ornithine and arginine in conjunction with the elevation of two common polyamines found in bacteria, putrescine and spermidine, in the *C. difficile* positive subjects further indicate increased bacterial activity. Investigations into polyamine function in bacteria have revealed that polyamine homeostasis is important for growth. Polyamines are also involved in a number of other functions, including their incorporation into the cell wall and biosynthesis of siderophores associated with the accumulation of iron. They are also important in acid resistance and can act as free radical ion scavengers.

Elevated Bilirubin Metabolites.

While bilirubin levels were similar between both groups, urobilinogen and D-urobilin were found to be higher in the positive samples compared to the negative samples. Bilirubin present in the intestines may be reduced to urobilinogen by bacteria including *C. difficile* and then further oxidized to urobilin. Consequently, higher levels of urobilinoids in the feces may represent increased bacterial activity especially from *C. difficile*. As observed in a random forest analysis, urobilinogen and D-urobilin were biochemicals that could be used for distinguishing between *C. difficile* positive and negative samples and may be suitable biomarkers for *C. difficile* infection. Further, these form the basis of spore-activating biochemicals and may form the basis of biomarkers of disease relapse in patients.

In certain embodiments the metabolites 5-aminovalerate, thymine, gamma-aminobutyrate (GABA), ammonia, N-acetylglutamate, agmatine, serine, N-acetylmuramate, X-16563, X-16071, X-15461 and/or X-15175 are used as biomarkers.

5-Aminovalerate.

Selenoproteins can be found in the genome of *Clostridium* species. Various selenoproteins are found within the D-proline reductase operon. The D-proline reductase operon is responsible for the reductive ring cleavage of D-proline into 5-aminovalerate. Thus, the presence of a bacterium comprising a D-proline reductase operon will result in an increase in 5-aminovalerate.

Thymine.

Thymine is one of the four nucleobases in DNA. Thymine is also known as 5-methyluracil, a pyrimidine nucleobase. As the name suggests, thymine may be derived by methylation of uracil at the 5th carbon.

Gamma-Aminobutyric Acid (GABA).

GABA is the chief inhibitory neurotransmitter in the mammalian central nervous system. It plays a role in regulating neuronal excitability throughout the nervous system. In humans, GABA is also directly responsible for the regulation of muscle tone. GABA is synthesized from glutamate using the enzyme L-glutamic acid decarboxylase and pyridoxal phosphate as a cofactor via a metabolic pathway called the GABA shunt. This process converts glutamate, the principal excitatory neurotransmitter, into the principal inhibitory neurotransmitter (GABA). GABA is catabolized by transaminase enzyme that catalyzes the conversion of 4-aminobutanoic acid and 2-oxoglutarate into succinic semialdehyde and glutamate. Succinic semialdehyde is then oxidized into succinic acid by succinic semialdehyde dehydrogenase and as such enters the citric acid cycle as a usable source of energy.

N-Acetylglutamate.

N-acetylglutamate (abbreviated NAcGlu) is biosynthesized from glutamic acid and acetyl-CoA by the enzyme N-acetylglutamate synthase. Arginine is the activator for this reaction. The reverse reaction, hydrolysis of the acetyl group, is catalyzed by a specific hydrolase. NAcGlu activates carbamoyl phosphate synthetase in the urea cycle.

Agmatine.

Agmatine ((4-aminobutyl)guanidine) is the decarboxylation product of the amino acid arginine and is an intermediate in polyamine biosynthesis. It is a putative neurotransmitter. It is stored in synaptic vesicles, accumulated by uptake, released by membrane depolarization, and inactivated by agmatinase. Agmatine binds to a2-adrenergic receptor and imidazoline binding sites, and blocks NMDA receptors and other cation ligand-gated channels. Agmatine inhibits nitric oxide synthase (NOS), and it induces the release of some peptide hormones.

Serine.

Serine is an amino acid. It is one of the proteinogenic amino acids. By virtue of the hydroxyl group, serine is classified as a polar amino acid. It is not essential to the human diet, since it is synthesized in the body from other metabolites, including glycine.

N-Acetylmuramate.

N-acetylmuramate (MurNAc), is the ether of lactic acid and N-acetylglucosamine. It is part of a biopolymer in the bacterial cell wall, built from alternating units of N-acetylglucosamine (GlcNAc) and N-acetylmuramic acid (MurNAc), cross-linked with oligopeptides at the lactic acid residue of MurNAc. This layered structure is called peptidoglycan.

X-16563, X-16071, X-15461, X-15175, and other metabolites designated with an "X" prefix are metabolites that form distinct peaks on LC/MS and are regarded as distinct unnamed biochemical variants. Identifying characteristics of these metabolites are available from Metabolon, Inc., Durham N.C. (metabolon.com).

Certain embodiments used a metabolome defined by compounds including metabolites having:

(i) p-value of less than 0.005 (5-aminovalerate, thymine, gamma-aminobutyrate (GABA), X-16563, X-16071, ammonia, agmatine, serine, N-acetylmuramate, X-15175, 5-methyluridine (ribothymidine), tryptamine, putrescine, X-15461, pyruvate, xanthine, 2-palmitoylglycerophosphoethanolamine, X-16271, methionine sulfoxide, allo-threonine, C-glycosyltryptophan, X-18557, 2-palmitoylglycerol (2-monopalmitin), uracil, deoxycholate, phenylacetylglycine, N-acetylglutamate, glutamate, glycerate, X-16301, 1-palmitoyl-GPE (16:0), X-15859, hexanoylglycine, X-18714, valerylglycine, urobilinogen, gamma-CEHC, 2-oxoadipate, X-15907, X-15519, 1H-quinolin-2-one, X-14400, X-16448, gamma-glutamyltyrosine, indole-3-carboxylic acid);

(ii) p value less than 0.05 (X-18270, 3-phenylpropionate (hydrocinnamate), N-acetylornithine, N-acetylserine, X-13510, gentisate, X-11521, X-11585, phenylpropionylglycine, 3-(4-hydroxyphenyl)propionate, X-17785, methionylisoleucine, decanoylcarnitine (C10), 3-methylthiopropionate, tetradecanedioate (C14), isoleucine, threonine, beta-hydroxyisovalerate, conjugated linoleate (18:2n7; 9Z,11E), diaminopimelate, xylose, leucyltryptophan, galactosamine, 4-imidazoleacetate, isocaproate, glucosamine, N6-carbamoylthreonyladenosine, X-14153, butyrylglycine (C4), X-18665, N-methylleucine, X-13230, X-11261, X-16654, phenylacetate, lanosterol, N-acetyltyrosine, isovalerylcarnitine (C5), phenylpyruvate, indolelactate, X-12889, prolylisoleucine, X-18718, X-11877, pyridoxate, riboflavin (Vitamin B2), X-15331, X-16278, N-acetylputrescine, X-12822, N-acetylmethionine, X-14255, pipecolate, X-16296, deoxycarnitine, beta-alanine, X-15431, 1-palmitoyl-GPI (16:0), eicosenoate (20:1n9 or 1n11), X-15454, gamma-glutamyl-valine, lithocholate, nicotinate, lysine, pregn steroid monosulfate, X-16444, isovalerate (C5), X-12450, X-16304, N-acetylmannosamine, succinate, 3-methylhistidine, gluconate, gamma-glutamylleucine, X-11718, taurocholate, fucose, X-15245, 2-stearoyl-GPC (18:0), fructose, X-09789, dehydroisoandrosterone sulfate (DHEA-S), X-11643, X-14928, X-16336, 13-methylmyristic acid, 2-palmitoyl-GPC (16:0), octanoylcarnitine (C8), isoleucylmethionine, X-17762, kynurenine, 3-methyl-2-oxovalerate, mevalonate, X-14900, X-17138, X-16684, dehydrolithocholate, X-13044, acetylcarnitine (C2), homocysteine, 3,4-dihydroxyhydrocinnamate, glutamine, X-17758, X-14421, alpha-hydroxyisovalerate, X-15503, X-13512, X-10346, glycyltryptophan, X-16117, N-acetylglycine, X-17453, X-17447, X-17305, N-acetylhistidine, X-14331, X-12685, X-14162, mesaconate (methylfumarate), proline, galactose, X-12410, 10-heptadecenoate (17:1n7), X-17674, pelargonate (9:0), X-13928, X-11945, hypoxanthine, X-12874, X-17150, X-18739, X-17543, taurochenodeoxycholate, X-17445, X-12100, X-17971, carnitine);

(iii) p value less than 0.1 (N-6-trimethyllysine, X-17706, asparagine, 4-methyl-2-oxopentanoate, X-17430, caprylate (8:0), X-11914, X-12746, N-acetylvaline, D-urobilin, arabinose, urate, uridine, X-16674, eicosapentaenoate (EPA; 20:5n3), delta-tocopherol, indoleacetate, valerate (5:0), palmitoyl sphingomyelin, pyridoxal, glucose, 3-ureidopropionate, X-12435, isoleucylvaline, X-15441, X-13850, X-14015, methionylleucine, 1-palmitoyl-GPC (16:0), X-17147, glycylisoleucine, 6-hydroxynicotinate, X-15426, X-15382, N-acetylphenylalanine, 1-oleoyl-GPE (18:1), X-15472, X-11412, rhamnose, X-16280, heptanoate (7:0), X-12812, X-15675, guanosine, cis-urocanate, sebacate (decanedioate), X-15486, X-15317, X-15497, beta-sitosterol, X-13536, X-14429, lysylleucine, X-14145, 1-oleoylglycerol (18:1), X-14383, X-11818, alanine, L-urobilin, maltotetraose, X-11452, propionylglycine, X-15484, X-12794, campesterol, X-11485, linoleamide (18:2n6), N-methylglutamate, X-14454, gamma-tocopherol, lysylisoleucine, X-12270, X-12101, X-15606, 8-aminocaprylate, X-12173, urea, vanillylmandelate (VMA), arabitol, glycocholate, palmitoylcarnitine (C16), stearoyl sphingomyelin, X-11540, X-16103, gamma-glutamylthreonine, X-16295, X-12770, X-11607, X-17984, X-11440, arginylleucine, X-11533, X-17910, anthranilate, N2-acetyllysine, alpha-glutamylglutamate);

(iv) p value less than 0.5 (X-17341, aspartate, quinolinate, X-18330, N-acetylglucosamine, docosahexaenoate (DHA; 22:6n3), X-14494, X-17250, gamma-glutamylphenylalanine, alpha-glutamylvaline, X-12944, urocanate, X-11906, 1-linoleoyl-GPC (18:2), X-14629, X-14606, indolepropionate, X-13883, arachidonate (20:4n6), dimethylglycine, X-15494, tryptophan, X-12824, gamma-glutamylisoleucine, X-17502, X-17846, X-16283, aspartylphenylalanine, X-14697, X-15853, X-16057, pyroglutamylvaline, X-18179, alanylvaline, 3-dehydrocholate, leucine, glutarate (pentanedioate), X-12040, adrenate (22:4n6), X-18294, X-13136, 3-aminoisobutyrate, docosapentaenoate (n6 DPA; 22:5n6), stearamide, X-12095, X-18309, leucylserine, X-12027, X-02249, erythronate, X-14096, tyramine, X-15371, cadaverine, homovanillate (HVA), caproate (6:0), X-17807, hexadecanedioate (C16), X-03056, X-17686, X-14392, 2-hydroxy-3-methylvalerate, docosatrienoate (22:3n3), X-14497, X-14155, inosine, X-11841, N6-acetyllysine, 3-hydroxybutyrate (BHBA), X-12379, X-17224, X-12114, X-11437, X-14365, X-12660, N-acetylleucine, methionine, X-13543, sarcosine (N-Methylglycine), valylisoleucine, X-12329, X-18167, vaccenate (18:1n7), X-18491, methylglutaroylcarnitine, cystine, X-18111, X-15168, 7-ketodeoxycholate, margarate (17:0), X-12026, 15-methylpalmitate, sertraline, X-15192, mannose, 3-methyl-2-oxobutyrate, X-14452, X-16033, thiamin (Vitamin B1), X-18333, X-12741, myo-inositol, rosuvastatin, X-11204, citramalate, X-17360, X-16685, X-15580, X-11538, lathosterol, N-carbamoylaspartate, X-11905, X-11684, X-17258, fumarate, 10-nonadecenoate (19:1n9), X-12237, N-acetylalanine, creatine, X-12851, N6-carboxyethyllysine, ribitol, palmitoleate (16:1n7), X-12830, 2-aminobutyrate, 2-deoxyribose, X-12028, thymidine, methylsuccinate, X-14396, glycocholenate sulfate, X-13005, aspartylleucine, isoleucylphenylalanine, X-16294, xylitol, X-11641, X-17784, alpha-glutamylthreonine, laurate (12:0), X-15515, valylglutamate, X-13671, ornithine, alpha-ketoglutarate, glycylvaline, X-12216, X-14406, X-11332, suberate (octanedioate), histidine, isoleucylisoleucine, oleamide, oleoyltaurine, X-16475, X-18291, 7-ketolithocholate, X-15697, X-15262, X-13152, N-methyl proline, xylonate, 7-methylguanine, X-14775, X-15189, X-15312, cysteine, X-12358, X-11827, dCMP, X-14524, X-17115, X-13834, arabonate, X-14517, gamma-glutamylalanine, dihomolinoleate (20:2n6), N-acetylproline, X-06126, 1-stearoyl-GPC (18:0), alanylisoleucine, X-12386, 3-hydroxyphenylacetate, X-16990, X-18278, 2-methylcitrate, X-12814, valine, X-15736, X-13723, 21-hydroxypregnenolone disulfate, isoleucylleucine, phosphoethanolamine (PE), dihomolinolenate (20:3n3 or 3n6), spermine, X-12051, X-14477, 1-oleoyl-GPC (18:1), X-14445, p-cresol sulfate, X-14320, 3-(4-hydroxyphenyl) lactate, adenine, X-17745, X-13879, N-acetyltryptophan, X-11838, X-15814, myristoleate (14:1n5), tauroursodeoxycholate, aspartate-glutamate, leucylglutamate, glycyltyrosine, 2-(4-hydroxyphenyl)propionate, N-acetylisoleucine, X-13529, X-17330, 3-hydroxyisobutyrate, creatinine, dehydrocholic acid, 4-hydroxyphenylacetate, glycerol 3-phosphate (G3P), kynurenate, hexanoylcarnitine (C6), X-15825, X-16803, N-acetylaspartate (NAA), X-11640, X-14700, 5,6-dihydrouracil, X-14333, X-11575, 1-palmitoylplasmenylethanolamine, ethanolamine, X-12803, leucylmethionine, X-15523, X-13446, X-11564, X-11578, 3-hydroxy-3-methylglutarate, X-16947, X-15522, nonadecanoate (19:0), valylleucine, cytosine, N-acetyl-beta-alanine, stearate (18: 0), threonate, X-13007, X-17463, phenol sulfate, X-18029, 1-stearoyl-GPI (18:0), caprate (10:0), alanylproline, 2-hydroxybutyrate (AHB), X-14269, X-12236, X-13582, X-17705, X-18307, N-acetylgalactosamine, 2-oleoyl-GPC (18:1), X-18041, isoleucylserine, X-16343, 4-androsten-3beta,17beta-diol disulfate 2, 2-oleoylglycerol (18:1), X-17969, X-14626, X-17010, X-16125, X-14628, ursodeoxycholate, X-18505, X-15999, docosapentaenoate (DPA; 22:5n3), X-15852, 7, 12-diketolithocholate, anserine, X-11722, X-11875, phenyllactate (PLA), X-11998, phenylalanine, myo-inositol hexakisphosphate, alpha-hydroxyisocaproate, N-acetylthreonine, X-13042, X-14384, X-17682, glycylphenylalanine, alpha-glutamyltyrosine, tricarballylate, X-12734, X-12726, X-11687, X-18370, pyridoxine (Vitamin B6), hydroxyproline, X-15030, 2-hydroxyisobutyrate, X-13733, 2, 3-butanediol, scyllo-inositol, inositol 1-phosphate (I1P), X-15854, X-14272, citrulline, phenethylamine, 12-dehydrocholate, X-12739, X-17398, X-12048, X-14496, X-17461, X-17470, X-08893, X-12820, X-12831, leucyltyrosine, glycerol, X-12039, X-12267, X-13742, X-17328, histidylisoleucine, X-14337, X-18331, X-14809, dihydrobiopterin, isoleucylglycine, 1-methylguanosine, 1,2-propanediol, glycylglycine, cholate, X-12465, glycerophosphoethanolamine, X-15532, X-17438, X-12748, X-18367, X-12850, prolylhydroxyproline, glycolithocholate sulfate, glycine, X-14448, X-17554, leucylalanine, cortolone, X-15572, orotate, X-17327, X-17759, X-17357, ribulose, X-13240, tyrosine, X-17335, N-palmitoyl taurine, X-13848, tetrahydrocortisone, pyroglutamine, X-12244, 1,3-diaminopropane, X-17315, 6'-sialyllactose, X-15689, dodecanedioate, X-11423, X-14318, X-12152, glucuronate, X-15841, nicotinate ribonucleoside, X-17692, 1-methylimidazoleacetate, N1-Methyl-2-pyridone-5-carboxamide, isoleucyltryptophan, X-17795, X-15483, X-11444, 1-eicosadienoyl-GPC (20:2), X-12511, X-11529, O-acetylhomoserine, glycochenodeoxycholate, X-14253, citrate, 2-methylbutyroylcarnitine (C5), ribose, X-17750, X-12749, X-14266, X-17552, X-12024, spermidine, X-14228, phenylalanylisoleucine, X-16626, X-18410, Isobar: hydantoin-5-propionate, N-carbamylglutamate, skatol, X-14539, 2-hydroxypalmitate, X-13689, 5-hydroxylysine, X-11272, pyrophosphate (PPi), xylulose, methylphosphate, 1-palmitoylglycerol (16:0), X-15401, X-12258, tryptophylleucine, azelate (nonanedioate; C9), phenethylamine (isobar with 1-phenylethanamine), phenylalanylleucine, serylleucine, X-15581, X-12230, 4-acetamidobutanoate, 2-aminopentanoate, X-15101, X-11984, X-17469, histidylleucine, X-11444, X-17359, X-15188, 3-(3-hydroxyphenyl)propionate, X-12059, leucylphenylalanine, glycoursodeoxycholate, X-17188, X-11542, X-17383, N2,N2-dimethylguanosine, leucylleucine, X-12398, X-12111, X-15363, X-17753, bilirubin, X-13528, X-18288, guanine, cyclo(leu-pro), X-13696, X-12804, succinylcarnitine (C4), taurolithocholate 3-sulfate, sorbitol, X-17848, adipate, X-12226, 2'-deoxyguanosine, X-17369, X-18165, X-18460, X-18555, X-18413, 4-hydroxyphenylpyruvate, X-14141, androsterone sulfate, glycylleucine, isoleucylglutamate, 6-oxolithocholate, 5alpha-pregnan-3beta,20alpha-diol disulfate), (v) p value less than 1.0 (histamine, X-17704, squalene, X-11407, X-13429, sorbose, X-11442, pseudouridine, X-16965, myo-inositol tetrakisphosphate (1,3,4,6 or 3,4,5,6 or 1,3,4,5), myo-inositol triphosphate (1,4,5 or 1,3,4), X-13719, leucylisoleucine, pyroglutamylglutamine, 4-hydroxycinnamate, X-14380, X-13885, X-11668, X-16397, lactose, X-17739, X-12107, dihydrocholesterol, X-14523, X-12127, X-12007, malate, undecanedioate, pentadecanoate (15:0), glycylproline, X-16468, homoserine (homoserine lactone), 1-stearoylglycerol (18:0), X-12234, threonylphenylalanine, X-12187, 1-methylhistidine, 5 alpha-androstan-3 alpha,17beta-diol disulfate, X-11396, X-18286, X-14302, 1-docosapentaenoylglycerophosphocholine, X-14404, X-12860, X-17549, 5 alpha-androstan-3beta, 17beta-diol disulfate, X-11333, X-14151, isoleucylalanine, prolylleucine, X-17676, X-18267, X-18279, alanylleucine, X-14196, X-07765, leucylglycine, X-17303, alanylphenylalanine, oleic ethanolamide, X-14951, X-17783, X-14708, tryptophan betaine, 1-heptadecanoyl-GPC (17:0), X-12310, X-17471, X-14224, thymidine 5'-monophosphate, uridine-2',3'-cyclic monophosphate, 3,4-dihydroxyphenylacetate, apiin, oleate (18:1n9), alpha-CEHC glucuronide, glutaroyl carnitine, hydroxyisovaleroyl carnitine, tiglyl carnitine, X-12813, X-12844, X-17185, stearoyl ethanolamide, X-16056, X-18292, X-12792, sphinganine, acetylphosphate, 2-hydroxystearate, X-13878, X-17348, X-17742, X-15869, X-11508, cholesterol, X-11561, X-13697, X-12189, X-15455, X-18164, X-16394, X-15579, X-17877, X-15916, X-13106, X-14056, X-14354, X-16391, X-12217, 2'-deoxyinosine, X-12093, X-15179, X-18702, sphingosine, X-12834, X-15634, X-18407, X-13741, X-14095, X-15609, X-16778, 1-stearoyl-GPE (18:0), 2-hydroxyglutarate, lactate, X-14658, X-14252, X-15708, X-15843, serylisoleucine, X-12211, tyrosylisoleucine, X-14596, X-13288, X-16830, X-17078, X-16013, methyl palmitate (15 or 2), X-15904, X-16946, chenodeoxycholate, X-12407, X-12846, X-13838, X-18456, X-13130, 3-hydroxydecanoate, N-acetylglutamine, X-12828, X-17790, X-14108, dimethylarginine (ADMA+SDMA), palmitate (16:0), X-15707, X-11787, 1-stearoylglycerophosphoglycerol, (R)-salsolinol, xanthurenate, allantoin, X-14525, 1-octadecanol, X-14632, X-18113, threonylleucine, X-15680, X-12092, X-12680, 2,3-dihydroxyisovalerate, X-13504, X-15526, pantothenate (Vitamin B5), X-12104, X-14848, X-15602, X-17062, X-13499, serylphenylalanine, X-15558, X-16627, X-14263, X-17299, X-12879, lignocerate (24:0), palmitoyl ethanolamide, malonate (propanedioate), N-acetylneuraminate, phenylalanylphenylalanine, myristate (14:0), glycerophosphorylcholine (GPC), X-15863, imidazole lactate, X-11334, X-17349, X-13844, X-14707, X-17626, X-12206, X-12231, cytidine, X-14057, X-17855, X-14662, alanylalanine, X-11530, arachidate (20:0), behenate (22:0), X-14097, X-15812, X-14195, X-15860, beta-hydroxypyruvate, X-12602, cystathionine, X-13239, X-12821, X-16480, X-11441, linolenate (18:3n3 or 3n6), X-17550, X-18273, phosphate, leucylproline, X-12805, X-12117, threitol, pregnen-diol disulfate, 5alpha-pregnan-3alpha,20beta-diol disulfate 1, X-14458, X-17145, X-12221, X-16681, 1-methyladenosine, N6-carboxymethyllysine, X-16580, X-12003, 2-linoleoylglycerol (2-monolinolein), X-17677, X-12689, X-14213, homocitrulline, valylglycine, isoleucyltyrosine, X-14193, X-15513, myo-inositol pentakisphosphate (1,2,4, 5,6 or 1,3,4,5,6), X-15850, 5-oxoproline, X-13451, X-17919, X-16302, X-12688, X-18272, X-14808, X-14624, X-15255, X-18275, X-14663, X-14954, X-15842, mannitol, biliverdin, X-12609, X-18349, X-15737, X-18554, X-15664, X-14314, X-13462, X-15563, X-18372, X-12742, taurine, X-12425, chiro-inositol, X-18271, X-16083, X-13994, X-13865, 2-hydroxyadipate, X-17559, X-12565, X-12110, X-12334, O-acetylserine, arginine, X-12195, phenylalanylserine, X-12411, tyrosylleucine, neopterin, X-17779, X-16975, X-15439, X-18332, X-14352, X-12215, X-18524, X-14904, X-12722, X-14007, X-14891, X-15559, 5,6-dihydrothymine, X-17717, sucralose, pinitol, X-16557, alpha-tocopherol, 3-dehydrocarnitine, X-15562, X-15415, X-14364, taurocholenate sulfate, linoleate (18:2n6), 4-androsten-3beta,17beta-diol disulfate 1, X-12263, 1,6-anhydroglucose, X-15754, X-18527, X-13706, X-14267, X-13835, X-16944, phenylacetylglutamine, stearoylcarnitine (C18), X-18693, X-18345, X-12170, X-14225, X-15743, N-formylmethionine, X-12712, X-13255, X-14709, X-15771, xanthosine, X-18368, X-11795), and (vi) p value of 1 (maltulose, trehalose, 2-phenylglycine, 3-pyridylacetate, 9,10-hydroxyoctadec-12(Z)-enoic acid, cyclo(leu-phe), fenofibrate, gamma-glutamylglutamate, gamma-glutamylglutamine, glutathione, oxidized (GSSG), mevalonolactone, N-hexanoyl-D-sphingosine, prostaglandin B2, VGAHAGEYGAEALER, vitexin, X-11832, X-13269, X-14385, X-16252, X-18523, vitexin, X-13445, X-13458, X-13734, X-17462, X-18565).

In certain embodiments 1, 2, 3, 4, 5, 6, 7, 8, 9, 10, 20, 30, 40, 50, 60, 70, 80, 90, 100, 200, 300, 400, 500, 600, 700, 800, 900, 1000 or more, including all values and ranges there between, of the metabolites listed can be measured and analyzed to identify and/or classify a subject with CDI.

A. Biomarker Measurement

In certain aspects, a biological sample can be processed to make it compatible with various analysis techniques to be employed in the detection and measurement of biomarkers in the sample. Processing can range from as little as no further processing to as complex as differential extraction and chemical derivatization. Extraction methods could include sonication, soxhlet extraction, microwave assisted extraction (MAE), supercritical fluid extraction (SFE), accelerated solvent extraction (ASE), pressurized liquid extraction (PLE), pressurized hot water extraction (PHWE) and/or surfactant assisted extraction (PHWE) in common solvents such as methanol, ethanol, mixtures of alcohols and water, or organic solvents such as ethyl acetate or hexane. In certain aspects liquid/liquid extraction is performed whereby non-polar metabolites dissolve in an organic solvent and polar metabolites dissolve in an aqueous solvent.

Extracted samples may be analyzed using any suitable method known in the art. Biological samples or extracts of biological samples can be analyzed on essentially any mass spectrometry platform, either by direct injection or following chromatographic separation. Typical mass spectrometers are comprised of a source that ionizes molecules within the sample, and a detector for detecting the ionized molecules or fragments of molecules. Non-limiting examples of common sources include electron impact, electrospray ionization (ESI), atmospheric pressure chemical ionization (APCI), atmospheric pressure photo ionization (APPI), matrix assisted laser desorption ionization (MALDI), surface enhanced laser desorption ionization (SELDI), and derivations thereof. Common mass separation and detection systems can include quadrupole, quadrupole ion trap, linear ion trap, time-of-flight (TOF), magnetic sector, ion cyclotron (FTMS), orbitrap, and derivations and combinations thereof. Ionization used in-line with liquid chromatography is referred to as Liquid Chromatography Mass Spectrometry (LC-MS). In certain aspects a mass spectrometer consisting of an electrospray ionization (ESI) source and linear ion-trap (LIT) mass analyzer is used.

The metabolites are generally characterized by their accurate mass, as measured by mass spectrometry technique used in the above method. The accurate mass may also be referred to as "accurate neutral mass" or "neutral mass". The accurate mass of a metabolite is given herein in Daltons (Da), or a mass substantially equivalent thereto. By "substantially equivalent thereto", it is meant that a +/−5 ppm difference in the accurate mass would indicate the same metabolite, as would be recognized by a person of skill in the art.

Data is collected during analysis and quantifying data for one or more than one metabolite is obtained. "Quantifying data" is obtained by measuring the levels or intensities of specific metabolites present in a sample. The quantifying data is compared to corresponding data from one or more than one reference sample. The "reference sample" is any suitable reference sample for the particular disease state. As would be understood by a person of skill in the art, more than one reference sample may be used for comparison to the quantifying data.

B. Identifying Biomarkers

The metabolomics approach described herein has enabled the inventors to quantify altered stool microbial and host cell responses in patients with a microbial infection. These findings complement metagenomic studies that have demonstrated gut microflora to be an important specificity determinant in colonic inflammation induced by microbial infections such as *C. difficile* infection. The inventors identify unique metabolomic signals that define host-microbial interactions. Global analytical networks of the CDI patient stool metabolome can be generated to identify and verify biomarkers for disease classification and progression.

Patterns in the stool metabolome across subjects with pathological conditions such as CDI, recurrent CDI and controls can be generated through the use of network visualization and analysis. Given the complex relationship between molecular and phenotype variables in disease patients. Towards that goal, the inventors collect appropriate stool data from patients and use networks to visualize and analyze the complex relationships to identify emergent patterns.

In certain aspects, metabolomics assays can be run using mass spectrometry. In further aspects, stool specimens can be tested using liquid and/or gas chromatography coupled to LTQ linear ion trap (LC-MS) and/or DSQ single quadrupole (GC-MS) mass spectrometry. Using this approach, the inventors have identified over 1,200 defined metabolites in patient stool samples. An estimate of the false discovery rate (q-value) is then calculated to take into account the multiple comparisons that normally occur in metabolomics based studies; as q-values have been reasonable for $p \leq 0.05$ in prior stool studies, no q-value cut off was established.

Data Analysis:

In certain aspects, data sets selected from normal and diseased subjects are analyzed using one or more of the following methods: (1) Separate bipartite networks to visualize the complex relationships between metabolites and patients for each of the groups of subjects. This analysis enables a comparison of the overall topological relationship between the groups; (2) Combined bipartite network of pooled groups, with nodes to represent the different groups. This analysis enables understanding of how the groups overlap in their metabolite profiles; (3) iCircos analysis can be used to explore the relationship between molecular and phenotype and demographic variables. This analysis enables an understanding of which variables are correlated with the metabolome profiles and subject groups. The overall goal of visual analyses is to enable the inventors to acquire an intuition of the molecular and phenotypic relationships in the data, while reducing the overhead and bias of assumptions inherent in most quantitative methods. This intuition has been shown to rapidly lead to insights about the underlying biological mechanisms involved in the disease. The visual patterns are then be used to guide the selection of quantitative methods whose assumptions match the patterns observed in the data.

Verifying:

In certain aspects patterns can be verified through graph-based and biostatistical methods. While the visual analyses often reveal unexpected patterns in the data, these patterns need to be verified using appropriate quantitative methods. The inventors use the visual patterns to guide selection of the appropriate quantitative methods to verify those patterns.

Network Validation:

Patterns from the visual analysis is validated in one or more steps: (i) Verification using quantitative methods whose assumptions match the patterns in the data. For example, if the data reveals disjointed clusters of patients or metabolites, then hierarchical clustering is used to identify the number and boundaries of clusters. However, if the network shows a nested structure, then a nested algorithm is used to identify the cluster boundaries; (ii) Verification of patient-metabolite-phenotype relationships. For example, if the patterns from the iCircos analysis suggest that certain races have a higher incidence of certain metabolites, then the inventors conduct appropriate significance tests (e.g., Kruskall-Wallis) to provide evidence for that pattern; (iii) Ingenuity Pathway Analysis can be used to verify biological relevance.

Descriptive statistics and pair-wise comparisons of metabolite abundance levels can be performed by t-test statistic using false discovery rate (FDR) adjustment for multiple comparisons. For skewed distributions (metabolite concentrations), the data is compared using nonparametric t tests (Kruskall-Wallis).

Translating:

In certain aspects the patterns are translated into approaches for classifying patients based on predictive models (classifiers), and for identifying new drug targets based on the inferred biological pathways. While verification provides a statistical foundation for classifying the patients, the findings can be further validated through the development of a classifier that combines key variables that classify patients in the clinic. This approach is to classify robust networks to distinguish clinical features in patients.

Data Analysis:

In certain aspects, the inventors select the most significant variables from the quantitative analysis to build a classifier. The classifier can be created using Multivariate Adaptive Regression Splines (MARS; a nonparametric modeling procedure using piecewise splines to model non-linearity and interactions amongst metabolites). Two approaches can be used for developing a panel of biomarkers that indicate a condition, e.g., CDI. First, a logistic regression approach can be utilized. Logistic Regression is a global parametric modeling process that estimates the probability of an event occurring as a linear function of profiles. In certain aspects, the probability of the binary outcome is modeled against a set of predictor variables and after adjustment for individual characteristics (e.g. race/ethnicity, demographics) is possible.

Performance can be analyzed by piece-wise regression modeling using multivariate adaptive regression splines (MARS). MARS is a nonparametric regression procedure that seeks to create a classification model based on piece-wise linear regressions. The results of MARS take the form of basis functions, which represent the predictors of disease state. Interpretation of the basis functions indicates the ranges over which particular metabolites contribute to the classification result. Model accuracy can be assessed and compared by the receiver operating characteristic curve (ROC). In certain aspects, the inventors identify and choose metabolite biomarkers that provide high accuracy evaluation using cross-validation misclassification error rates. In addition, the inventors can use available tools such as Ingenuity Pathways Analysis to identify biological pathways that are activated in the patients, and that can be a potential target for known drugs that could be effective.

Outcomes:

Early diagnosis of CDI in patients is useful for optimal clinical management and improved prognosis. The high frequency of CDI coupled with poor clinical outcomes for cases not promptly and effectively treated, makes clear the necessity for rapid and accurate detection.

II. CLASSIFICATION AND DIAGNOSIS

For many studies, two types of statistical analysis are usually performed: (1) significance tests and (2) classification analysis. (1) For pair-wise comparisons, the inventors typically perform Welch's t-tests and/or Wilcoxon's rank sum tests. For other statistical designs, various ANOVA procedures may be performed (e.g., repeated measures ANOVA). (2) For classification, random forest analyses were primarily used. Random forests give an estimate of how well one can classify individuals in a new data set into each group, in contrast to a t-test, which tests whether the unknown means for two populations are different or not.

Random forests create a set of classification trees based on continual sampling of the experimental units and compounds. Then each observation is classified based on the majority votes from all the classification trees. Statistical analyses are performed with the program "R" (see URL cran.r-project.org).

The statistical method used for logistic regression-based classification is called elastic-net regularized generalized linear models (Friedman et al. 2009). The basic idea is to find a linear model of the selected variables, such that if the resulting functional output is lower than 0, the prediction is infected; if the output is greater than 0, the prediction is not infected or vice versa; the coding of the 0 vs. 1 is irrelevant to the algorithm.) Once an initial model with selected variables was chosen, models were tested for (out-of-sample) predictive accuracy with models built from different subsets of the chosen variables along with variables chosen by other models (such as Random Forest Prediction). Out-of-sample accuracy was calculated using 5-fold cross-validation (See Chapter 7 of Hastie et al. The Elements of Statistical Learning (2009)).

t-Tests:

t-tests test whether the unknown means for two populations are different or not. The p-value gives the amount evidence that the population means are different based on the data (through the t-statistic). The smaller the p-value, the more evidence that the population means are different. Often, a significance level of 0.001, 0.005, 0.01, or 0.05 is used. When the p-value is less than 0.05, there is enough evidence to conclude that the population means are different ("statistical significance"). The level of 0.05 is the false positive rate. This means that 5% of the time, the t-test would incorrectly conclude the population means are different when they are actually the same.

q-Values:

The level of 0.05 is the false positive rate when there is one test. However, for a large number of tests we need to account for false positives. If the data were simply random noise, approximately 5% of the p-values would be less than 0.05, 10% of the p-values would be less than 0.10, etc. Thus, even if the data were only random noise, we would get approximately 10 "significant" results out of 200 compounds when the false positive rate is 0.05.

There are different methods to correct for multiple testing. The oldest methods are family-wise error rate adjustments (Bonferroni, Tukey, etc.), but these tend to be extremely conservative for a very large number of tests. With gene arrays, using the False Discovery Rate (FDR) is more common. The family-wise error rate adjustments give one a high degree of confidence that there are zero false discoveries. However, with FDR methods, one can allow for a small number of false discoveries. The FDR for a given set of compounds can be estimated using the q-value (see Storey J and Tibshirani R. 2003, Statistical significance for genomewide studies. *Proc. Natl. Acad. Sci. USA* 100: 9440-9445).

To interpret the q-value, first sort the data by the p-value then choose the cutoff for significance (typically p<0.05). The q-value gives the false discovery rate for the selected list (i.e., an estimate of the proportion of false discoveries for the list of compounds whose p-value is below the cutoff for significance).

Random Forest:

Random forest is a supervised classification technique based on an ensemble of decision trees (see Breiman. 2001. *Machine Learning*. 45:5, for the original description; Goldstein et al. 2010. *BMC Genetics*. 11:49, for additional information). For a given decision tree, a random subset of the data with identifying true class information is selected to build the tree ("bootstrap sample" or "training set"), and then the remaining data, the "out-of-bag" (OOB) variables, are passed down the tree to obtain a class prediction for each sample. This process is repeated thousands of times to produce the forest. The final classification of each sample is determined by computing the class prediction frequency ("votes") for the OOB variables over the whole forest. For example, suppose the random forest consists of 50,000 trees and that 25,000 trees had a prediction for sample 1. Of these 25,000, suppose 15,000 trees classified the sample as belonging to Group A and the remaining 10,000 classified it as belonging to Group B. Then the votes are 0.6 for Group A and 0.4 for Group B, and hence the final classification is Group A. This method is unbiased since the prediction for each sample is based on trees built from a subset of samples that do not include that sample. When the full forest is grown, the class predictions are compared to the true classes, generating the "OOB error rate" as a measure of prediction accuracy. Thus, the prediction accuracy is an unbiased estimate of how well one can predict sample class in a new data set.

To determine which variables (biochemicals) make the largest contribution to the classification, a "variable importance" measure is computed. The inventors use the "Mean Decrease Accuracy" (MDA) as this metric. The MDA is determined by randomly permuting a variable, running the observed values through the trees, and then reassessing the prediction accuracy. If a variable is not important, then this procedure will have little change in the accuracy of the class prediction (permuting random noise will give random noise). By contrast, if a variable is important to the classification, the prediction accuracy will drop after such a permutation, which is recorded as the MDA. Thus, the random forest analysis provides an "importance" rank ordering of biochemicals; the inventors typically output the top 30 biochemicals in the list as potentially worthy of further investigation.

Certain embodiments of the present invention provide methods of diagnosing CDI in a subject comprising one or more of the following steps: (a) obtaining a sample from the subject; (b) determining a metabolite profile for the subject's sample by measuring the amount of each of one or more metabolite biomarkers; (c) comparing the subject's metabolite profile to a healthy control metabolite profile for the same one or more metabolite biomarkers in each sample or comparing biomarker levels to a reference; and (d) identifying differences between the subject's metabolite profile and the healthy control or reference metabolite profile; wherein an increase or decrease in the level of one or more metabolite biomarkers in the subject's metabolite profile as compared to the healthy control or reference metabolite profile indicates CDI in the subject.

III. METHODS OF TREATING CDI

*C. difficile* treatment is complicated by the fact that antibiotics trigger *C. difficile* associated disease. Nevertheless, antibiotics are the primary treatment option at present. Antibiotics least likely to cause *C. difficile* associated disease are vancomycin and metronidazole. Vancomycin resistance evolving in other microorganisms is a cause for concern in using this antibiotic for treatment, as it is the only effective treatment for infection with other microorganisms (Gerding, *Curr. Top. Microbiol. Immunol.* 250:127-39, 2000). Antibiotics for treating *C. diff* include metronidazole, vancomycin, fidaxomicin, rifampicin, rifaximin, nitazoxanide or rifabutin used singly or in combinations.

Probiotic therapies include administering non-pathogenic microorganisms that compete for niches with the pathogenic bacteria. For example, treatment of *C. diff* with a combination of vancomycin and *Saccharomyces boulardii* has been reported (McFarland et al., JAMA., 271(24):1913-8, 1994. Erratum in: JAMA, 272(7):518, 1994). A probiotic composition can comprise a microorganism selected from *Lactobacilli, Bifidobacteria, E. coli, Eubacteria, Saccharomyces* species, Enterococci, *Bacteroides* or non-pathogenic Clostridia, e.g. *Clostridium butyricum* and non-pathogenic *Clostridium difficile*. As will be appreciated by one of skilled in the art, other suitable probiotics known in the art may also be used.

Other therapies include administering therapeutic antibodies. Therapeutic antibodies include those antibodies that bind and inhibit *C. difficile* or *C. difficile* toxins, the inhibition of which provides a therapeutic benefit.

The network visualization and quantitative analysis of the CDI metabolome has identified a novel nutraceutical strategy in CDI, phytic acid supplementation. Phytic acid (known as inositol hexakisphosphate (IP6), or phytate when in salt form) is the principal storage form of phosphorus in many plant tissues, especially bran and seeds. Phytate is not digestible to humans or non-ruminant animals. Catabolites of phytic acid are called lower inositol polyphosphates. Examples are inositol penta-(IP5), tetra-(IP4), and triphosphate (IP3). In certain aspects phytic acid supplementation can include administering phytic acid or other inositol polyphosphates or their derivatives. The inventors identified phytic acid supplementation as a treatment for *C. difficile* infection.

IV. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Biochemical Differences in Fecal Samples from Individuals that Tested Positive for *Clostridium difficile* Compared to Those Who Tested Negative.

This study was conducted to characterize the biochemical differences in human fecal samples collected from individuals that tested positive for *Clostridium difficile* compared to those who tested negative. For this study, 55 human fecal samples from infected (31) and non-infected (24) individuals were analyzed. Raw data from each sample were entered into a spreadsheet in Excel format with no additional normalizations prior to statistical analysis.

Global biochemical profiles were compared across two treatment groups: *C. difficile* infected (POS) and uninfected (NEG). Fifty-five human fecal matter samples were processed for metabolomics analysis. Samples were inventoried and immediately stored at −80° C. At the time of analysis samples were extracted and prepared for analysis using Metabolon's standard solvent extraction method. The extracted samples were split into equal parts for analysis on the GC/MS and LC/MS/MS platforms. Also included were several technical replicate samples created from a homogeneous pool containing a small amount of all study samples (Matrix samples).

Two purified standards of inositol hexakisphosphate were also submitted for extraction and processing across the metabolomics platform. The data associated with the two standards shows the identification of a number of inositol phosphate related compounds including myo-inositol; myo-inositol 1,4-bisphosphate; myo-inositol triphosphate; myo-inositol tetrakisphosphate; myo-inositol pentakisphosphate; and myo-inositol hexakisphosphate. *C. difficile* toxins A and B belong to the family of clostridial glucosylating toxins, which inactivate eukaryotic GTPases of the Rho family by attachment of glucose. Previous studies have shown that once these toxins (A and B) are translocated into the cytosol of target cells, processing of the toxin occurs by autocatalytic cleavage that is enhanced by inositol hexakisphosphate. It is interesting to note that myo-inositol hexakisphosphate was detected at low levels in all CDI patient specimens. One hypothesis is that subjects with elevated levels of myo-inositol hexakisphosphate may represent individuals with a diminished sensitivity to *C. difficile* toxins. The lack of significant levels to neutralize toxin activity in *C. difficile*-positive subjects suggests that this compound may not be readily bioavailable in *C. difficile* patients; alternatively, a lack of bioavailability may be a suitable indicator of *C. difficile* susceptibility or sensitivity.

Several of the biochemicals utilized by the analysis are listed above. Biomarkers identified by bipartite and cross-validated out-of-sample error rate analysis include metabolites associated with nitrogen metabolism (ammonia and GABA), polyamine metabolism (putrescine and agmatine), bile acid metabolites, and bacterial N-acetylation of several metabolite classes.

B. Indicators of Inflammation in *C. difficile*-Positive Samples

*C. difficile* is known to be the primary causative agent for pseudomembranous colitis, and indicators of inflammation were associated with the positive samples. These included higher levels of citrulline, which may be generated from arginine via iNOS as well as higher levels of arachidonate (though not statistically significant), which can be used as a source for COX enzyme conversion to prostaglandins. There were also higher levels of hypoxanthine and xanthine in positive subjects, which may be an indication of an elevated level of xanthine oxidase activity and increased oxidative stress in the positive subjects that may also contribute to inflammation and colitis. Patients identified with elevated levels of stool inflammatory mediators may be prescribed anti-inflammatory therapy to alleviate clinical symptoms in this subgroup.

C. Metabolomics Platform

Sample Accessioning:

Each sample received was accessioned into the Metabolon LIMS system and was assigned by the LIMS a unique identifier, which was associated with the original source identifier only. This identifier was used to track all sample handling, tasks, results, etc. The samples (and all derived aliquots) were bar-coded and tracked by the LIMS system. All portions of any sample were automatically assigned their own unique identifiers by the LIMS when a new task was created; the relationship of these samples was also tracked. All samples were maintained at −80° C. until processed.

Sample Preparation:

Sample preparation was carried out using the automated MicroLab STAR® system from Hamilton Company. Recovery standards were added before the first step in the extraction process for QC purposes. Sample preparation was conducted using, for example, a series of organic and aqueous extractions to remove the protein fraction while allowing maximum recovery of small molecules. The resulting extract was divided into two fractions: (1) for analysis by LC and (2) for analysis by GC. Samples were placed briefly on a TurboVap® (Zymark) to remove the organic solvent. Each sample was then frozen and dried under vacuum. Samples were then prepared for the appropriate instrument, either LC/MS or GC/MS.

QA/QC:

For QA/QC purposes, a number of additional samples are included with each day's analysis. Furthermore, a selection of QC compounds is added to every sample, including those under test. These compounds are carefully chosen so as not to interfere with the measurement of the endogenous compounds. Tables 1 and 2 describe the QC samples and compounds. These QC samples are primarily used to evaluate the process control for each study as well as aiding in the data curation.

Gas Chromatography/Mass Spectrometry (GC/MS):

The samples destined for GC/MS analysis were re-dried under vacuum desiccation for a minimum of 24 hours prior to being derivatized under dried nitrogen using bistrimethyl-silyl-trifluoroacetamide (BSTFA). The GC column was 5% phenyl, and the temperature ramp is from 40° to 300° C. in a 16 minute period. Samples were analyzed on a Thermo-Finnigan Trace DSQ fast-scanning single-quadrupole mass spectrometer using electron impact ionization. The instrument was tuned and calibrated for mass resolution and mass accuracy on a daily basis. The information output from the raw data files was automatically extracted as discussed below.

Accurate Mass Determination and MS/MS Fragmentation (LC/MS), (LC/MS/MS):

The LC/MS portion of the platform was based on a Waters ACQUITY UPLC and a Thermo-Finnigan LTQ-FT mass spectrometer, which had a linear ion-trap (LIT) front end and a Fourier transform ion cyclotron resonance (FT-ICR) mass spectrometer backend. For ions with counts greater than 2 million, an accurate mass measurement could be performed.

TABLE 1

Description of QC Samples

| Type | Description | Purpose |
|---|---|---|
| MTRX | Large pool of human plasma maintained by Metabolon that has been characterized extensively. | Assure that all aspects of Metabolon process are operating within specifications. |
| CMTRX | Pool created by taking a small aliquot from every customer sample. | Assess the effect of a non-plasma matrix on the Metabolon process and distinguish biological variability from process variability. |
| PRCS | Aliquot of ultra-pure water | Process Blank used to assess the contribution to compound signals from the process. |
| SOLV | Aliquot of solvents used in extraction. | Solvent blank used to segregate contamination sources in the extraction. |

TABLE 2

QC Standards

| Type | Description | Purpose |
|---|---|---|
| DS | Derivatization Standard | Assess variability of derivatization for GC/MS samples. |
| IS | Internal Standard | Assess variability and performance of instrument. |
| RS | Recovery Standard | Assess variability and verify performance of extraction and instrumentation. |

Liquid Chromatography/Mass Spectrometry (LC/MS):

The LC/MS portion of the platform was based on a Waters ACQUITY UPLC and a Thermo-Finnigan LTQ mass spectrometer, which consisted of an electrospray ionization (ESI) source and linear ion-trap (LIT) mass analyzer. The sample extract was split into two aliquots, dried, and then reconstituted in acidic or basic LC-compatible solvents, each of which contained 11 or more injection standards at fixed concentrations. One aliquot was analyzed using acidic positive ion optimized conditions and the other using basic negative ion optimized conditions in two independent injections using separate dedicated columns. Extracts reconstituted in acidic conditions were gradient eluted using water and methanol both containing 0.1% formic acid, while the basic extracts, which also used water/methanol, contained 6.5 mM ammonium bicarbonate. The MS analysis alternated between MS and data-dependent $MS^2$ scans using dynamic exclusion.

Accurate mass measurements could be made on the parent ion as well as fragments. The typical mass error was less than 5 ppm. Ions with less than two million counts require a greater amount of effort to characterize. Fragmentation spectra (MS/MS) were typically generated in data dependent manner, but if necessary, targeted MS/MS could be employed, such as in the case of lower level signals.

Bioinformatics:

The informatics system consisted of four major components, the Laboratory Information Management System (LIMS), the data extraction and peak-identification software, data processing tools for QC and compound identification, and a collection of information interpretation and visualization tools for use by data analysts. The hardware and software foundations for these informatics components were the LAN backbone, and a database server running Oracle 10.2.0.1 Enterprise Edition.

LIMS:

The purpose of the LIMS system is to enable fully auditable laboratory automation through a secure, easy to use, and highly specialized system. The scope of the LIMS system encompasses sample accessioning, sample preparation, and instrumental analysis, reporting, and advanced data analysis. All of the subsequent software systems are grounded in the LIMS data structures. It has been modified to leverage and interface with the in-house information extraction and data visualization systems, as well as third party instrumentation and data analysis software.

Data Extraction and Quality Assurance:

The data extraction of the raw MS data files yielded information that could be loaded into a relational database and manipulated without resorting to BLOB manipulation. Once in the database, the information was examined and appropriate QC limits were imposed. Peaks were identified using peak integration software, and component parts were stored in a separate and specifically designed complex data structure.

Compound Identification:

Compounds were identified by comparison to library entries of purified standards or recurrent unknown entities. Identification of known chemical entities was based on comparison to library entries of purified standards. More than 1000 commercially available purified standard compounds have been registered into LIMS for distribution to both the LC and GC platforms for determination of their analytical characteristics. The combination of chromatographic properties and mass spectra gave an indication of a match to the specific compound or an isobaric entity. Additional entities could be identified by virtue of their recurrent nature (both chromatographic and mass spectral). These compounds have the potential to be identified by future acquisition of a matching purified standard or by classical structural analysis.

Curation:

A variety of curation procedures were carried out to ensure that a high quality data set was made available for statistical analysis and data interpretation. The QC and curation processes were designed to ensure accurate and consistent identification of true chemical entities, and to remove those representing system artifacts, mis-assignments, and background noise. Visualization and interpretation software is used to confirm the consistency of peak identification among the various samples. Library matches for each compound were checked for each sample and corrected if necessary.

Normalization:

For studies spanning multiple days, a data normalization step was performed to correct variation resulting from instrument inter-day tuning differences. Essentially, each compound was corrected in run-day blocks by registering the medians to equal one (1.00) and normalizing each data point proportionately (termed the "block correction"). For studies that did not require more than one day of analysis, no normalization is necessary, other than for purposes of data visualization.

Statistical Calculation:

For many studies, two types of statistical analysis are usually performed: (1) significance tests and (2) classification analysis. (1) For pair-wise comparisons, the inventors typically perform Welch's t-tests and/or Wilcoxon's rank sum tests. For other statistical designs, various ANOVA procedures may be performed (e.g., repeated measures ANOVA). (2) For classification, random forest analyses were primarily used. Random forests give an estimate of how well one can classify individuals in a new data set into each group, in contrast to a t-test, which tests whether the unknown means for two populations are different or not. Random forests create a set of classification trees based on continual sampling of the experimental units and compounds. Then each observation is classified based on the majority votes from all the classification trees. Statistical analyses are performed with the program "R" (see URL cran.r-project.org).

The statistical method used for logistic regression-based classification is called elastic-net regularized generalized linear models (Friedman et al. 2009). The basic idea is to find a linear model of the selected variables, such that if the resulting functional output is lower than 0, the prediction is infected; if the output is greater than 0, the prediction is not infected or vice versa; the coding of the 0 vs. 1 is irrelevant to the algorithm.) Once an initial model with selected variables was chosen, models were tested for (out-of-sample) predictive accuracy with models built from different subsets of the chosen variables along with variables chosen by other models (such as Random Forest Prediction). Out-of-sample accuracy was calculated using 5-fold cross-validation (See Chapter 7 of Hastie et al. The Elements of Statistical Learning (2009)).

The invention claimed is:

1. A method of treating a subject having a *Clostridium difficile* infection (CDI) comprising:
    measuring levels of gamma-aminobutyrate (GABA), ammonia, or GABA and ammonia, in a stool sample from a subject; and
    administering a treatment for CDI to the subject if the levels of the one or more biomarkers are elevated compared to a reference level.

2. The method of claim 1, wherein the treatment of CDI includes administering metronidazole, vancomycin, fidaxomicin, rifampicin, rifaximin, nitazoxanide, rifabutin, or combinations thereof.

3. The method of claim 1, wherein the treatment of CDI includes administering a probiotic therapy.

4. The method of claim 1, wherein the treatment of CDI includes administering phytic acid or derivatives thereof.

5. A method of treating a subject having a recurrent *Clostridium difficile* infection (CDI) comprising:
    distinguishing a subject having recurrent *Clostridium difficile* infection from a subject having a non-recurrent *Clostridium difficile* infection comprising measuring levels of one or more biomarkers selected from ammonia or gamma-aminobutyrate (GABA) in a stool sample and identifying a subject having a recurrent CDI if one or more biomarkers are elevated more than 200% compared to a non-infected control level; and
    administering a treatment for CDI to the subjects identified as having recurrent CDI.

6. The method of claim 5, wherein the biological sample is a stool sample.

* * * * *